United States Patent
Taylor et al.

(10) Patent No.: US 12,422,424 B1
(45) Date of Patent: Sep. 23, 2025

(54) ADDITIVE MANUFACTURING TEST METHOD FOR METALLIC ALLOY COMPOSITIONS AND METHODS OF MAKING THE SAME

(71) Applicant: Tailored Alloys LLC, Horizon City, TX (US)

(72) Inventors: Hunter Taylor, Horizon City, TX (US); Laszlo Kecskes, Havre de Grace, MD (US)

(73) Assignee: Tailored Alloys, LLC, Horizon City, TX (US)

( * ) Notice: Subject to any disclaimer, the term of this patent is extended or adjusted under 35 U.S.C. 154(b) by 563 days.

(21) Appl. No.: 17/345,376

(22) Filed: Jun. 11, 2021

(51) Int. Cl.
| | |
|---|---|
| *G01N 33/2045* | (2019.01) |
| *B22F 10/28* | (2021.01) |
| *B22F 10/38* | (2021.01) |
| *B29C 64/00* | (2017.01) |
| *B29C 64/10* | (2017.01) |
| *B33Y 10/00* | (2015.01) |

(52) U.S. Cl.
CPC ......... *G01N 33/2045* (2019.01); *B22F 10/28* (2021.01); *B22F 10/38* (2021.01); *B29C 64/00* (2017.08); *B29C 64/10* (2017.08); *B33Y 10/00* (2014.12)

(58) Field of Classification Search
CPC ........... B22F 10/28; B22F 10/38; B29C 64/00
See application file for complete search history.

(56) References Cited

PUBLICATIONS

JK Lasers, (JK Fiber Lasers), pre-2012 (Year: 2012).*
H. Zhang, Y. Zhao, S. Huang, S. Zhu, F. Wang, D. Li, Manufacturing and analysis of high-performance refractory high-entropy alloy via selective laser melting, Materials 2019, 12, 720 (Year: 2019).*
SLM-Solutions, SLM-500, https://www.slm-solutions.com/products-and-solutions/machines/slm-500/, Nov. 27, 2020 (Year: 2020).*
Ewald, Simon, et al., "Rapid Alloy Development of Extremely High-Alloyed Metals Using Powder Blends in Laser Powder Bed Fusion," Materials 2019, 12, 1706, www.mdpi.com/journal/materials.
Roehling, John D., et al., "Rapid Solidification in Bulk Ti—Nb Alloys by Single-Track Laser Melting," JOM, vol. 70, No. 8, 2018, The Minerals, Metals & Materials Society, pp. 1589-1597.

* cited by examiner

*Primary Examiner* — Jonathan Johnson
(74) *Attorney, Agent, or Firm* — HILL, KERTSCHER & WHARTON, LLP; Gregory T. Ourada

(57) ABSTRACT

The present disclosure relates to a fabrication and evaluation process for testing new metallic alloy chemistries and compositions for laser powder bed fusion (L-PBF). The new methodology is efficient and effective for new compositions with a minimal investment of generating large quantities of powder feedstock for required in conventional AM processing. The method allows for subsurface melting of the new alloy composition by varying the depth of penetration by a control of the input power level, power deposition rate, and rastering scan strategy. Post-mortem analysis of the subsurface microstructure permits an analysis of the durability and suitability of the new metallic alloy for this manufacturing mode. The method utilizes available infrastructure, technology, and characterization techniques.

20 Claims, 10 Drawing Sheets

3(A)

3(B)

4(A)

4(B)

4(C)

4(D)

6(A)

6(B)

ADDITIVE MANUFACTURING TEST METHOD FOR METALLIC ALLOY COMPOSITIONS AND METHODS OF MAKING THE SAME

BACKGROUND OF THE INVENTION

Field of the Invention

The present disclosure relates to methods of evaluating the chemistry of an alloy for its suitability for melt based additive manufacturing without the need to render the alloy to a powder feedstock.

Description of Related Art

Over the past 30 years, many additive manufacturing (AM) approaches have been invented. These include material extrusion, vat photopolymerization, directed energy deposition, sheet lamination, binder jetting, material jetting, and powder bed fusion. Of these methods, we demonstrate the utility of the methods of the present disclosure described herein using the Laser Powder Bed Fusion (L-PBF) mode. However, it will be appreciated that both the spirit of this disclosure and the methodology may be applicable to all AM modes that rely on a powder feedstock to create the fabricated article, part, or build.

In the L-PBF process, a high energy laser beam is selectively scanned across bed containing a layer of powder while the energy of the laser beam and the scanning velocity are controlled. The powder bed is incrementally lowered in some prescribed manner (i.e., stepwise or continuously) while fresh powder is spread on top of the previous layer. As the laser beam moves spatially in a controlled, pre-programmed fashion, powder particles in the topmost layers fuse to the layers beneath it.

In particular, current practice in AM alloy feedstock development entails a mostly empirical time- and labor-intensive evaluation of the new alloy composition directly in a L-PBF system. Once a new powder feedstock is available in sufficient quantity, test articles are printed and subsequently evaluated under a broad range of printing conditions. This sequence is iterated until the correct set of print parameters are identified to fabricate a minimal defect part. For the purposes of this disclosure, a minimal defect part means an article that lacks internal flaws which may include voids, large cracks, compositionally segregated and non-uniform regions, and, most importantly, morphologically non-uniform substructures that prevent adoption due to inadequate and/or substandard material properties. These substructures may be crystallographic subunits or grains separated by grain boundaries that may contain other phases, more commonly known as clusters and precipitates.

While the trial-and-error evaluation process provides highly valuable information about the set of conditions necessary for viable part fabrication procedures, these iterations do not differentiate between the effect of material properties intrinsic to the specific alloy composition and those that only relate to the scan rates, dwell times, and strategies, as well as the laser power input parameters available in the L-PBF system. That is, the inherent coupling of these factors renders it difficult to separate out the intrinsic nature of the new alloy such as its phase composition, ductility, brittleness, microstructural evolution under very large thermal gradients, or sensitivity to cracking due to rapid heating and cooling cycles.

New metallic alloy development for laser powder bed fusion (L-PBF) is also hindered by extremely high costs to create sufficient quantities of powder feedstock of a new composition to fully test. In addition to cost, the availability of equipment to create the powder feedstock is limited.

Accordingly, a new method is needed that independently provides this information without being affected by the geometric constraints or other factors that exist during the AM build process.

While alternative methods wherein test coupons have been fabricated from the parent composition by conventional melt-casting are less costly, they are also inadequate. This is because these methods do not represent the same thermal history as that seen in the L-PBF process.

New metallic alloy development for AM via the application of its various modes, e.g., laser powder bed fusion (L-PBF), is hindered by the extremely high costs to create larger quantities of powder feedstocks of the new alloy composition for fabrication, testing, and evaluation. Moreover, these costs are further exacerbated by the scarcity and availability of suitable inert-gas powder atomization equipment to create them. Accordingly, there remains a need for an efficient method of determining the suitability of an alloy for melt-based additive manufacturing without the need to render the alloy into a powder feedstock.

Herein, we disclose a new methodology that is both low-cost and high-throughput utilizing readily available technology. More importantly, one of the advantages of this method is that the thermal history of the parent material composition subjected to this procedure is highly similar to those seen during the 3D printing process.

Specifically, the disclosed method may be applied to materials comprising a combination of metallic and non-metallic elements, referred to herein as alloys.

SUMMARY OF THE INVENTION

The present disclosure generally includes a method of assessing the suitability of an alloy for use in melt-based additive manufacturing without the need to render the alloy to a powder feedstock.

In general terms, the method of the present disclosure to evaluate the chemical composition of an alloy for suitability for melt based additive manufacturing, includes the general steps: (a) obtaining a alloyed article or coupon of a chemical composition and melting at a first energy level the surface and a first subsurface volume of the alloyed coupon, such that the first subsurface volume has a first depth; (b) permitting the pre-alloyed coupon to cool below its melting point so as to create a cooled first subsurface volume having first set of structural qualities; (c) re-melting the surface and a second subsurface volume of a second depth less than the first depth; (d) permitting the pre-alloyed coupon to cool below melting so as to create a cooled second subsurface volume having second structural qualities; and (e) evaluating the first structural qualities and second structural qualities to determine whether alloys of such chemical composition may be rendered into power feedstock for use in melt-based additive manufacturing. Note, this methodology can be extended to the heating and re-heating of more than two subsurface volumes and their subsequent analyses of their qualities.

In some embodiments the test articles or coupons are flat, though other surfaces may be used. In other embodiments, the test articles or coupons may be created as a pre-alloyed button using powder feedstock.

The present disclosure includes a wide variety of embodiments that may include the creation of a series of subsurface volumes as described in steps (a)-(d) that may include the creation of multiple (i.e., two or more) subsurface volumes in an overlapping array at corresponding different depths from the coupon surface. Several such arrays of subsurface volumes representing the treatment with different energy levels may also be distributed at various locations over a given surface of a pre-alloyed article or coupon so as to create a matrix of test subsurface volumes to permit the assessment of characteristics of each such subsurface volume as well as the characteristics of the interfaces between adjacent test subsurface volumes. It will be appreciated that the method of the present disclosure may be carried out by determining a plurality of locations over a given surface of a pre-alloyed article or coupon, and determining initial and successive power levels to be applied at each such location. For instance, the treatment with different energy levels may form at least three subsurface volumes at depths D1, D2 and D3 (D3 being less than D2 and D2 being less than D1) at a first location, and at least two subsurface volumes at different depths D4 and D5 (D5 being less than D4) at a second location representing test subsurface volumes created at different initial and successive power levels. When iterated, the procedure described in this embodiment permits the operator to create a matrix of a large number of test subsurface volumes permitting the evaluation of characteristics of each such subsurface volume as well as the characteristics of the interfaces between adjacent test subsurface volumes to determine whether the structural qualities of alloys of its chemical composition may be rendered into power feedstock for use in melt-based additive manufacturing. It will be appreciated that variations of the method of the present disclosure thus may include creating arrays of test subsurface volumes that may comprise a plurality of subsurface volumes at depths D1, D2 and D3, etc. (D3 being less than D2 and D2 being less than D1, etc.) at a first location, and a plurality of subsurface volumes at different depths D4 and D5, etc. (D5 being less than D4, etc.) at a second location, etc. so as to create a test array representative of a large matrix of energy levels and associated test volume sets from which characteristic measurement data may be obtained. Such an array of a plurality of test subsurface volumes created at different initial and successive power levels representing the treatment with different energy levels may also be distributed at various locations over a given surface of a pre-alloyed article or coupon so as to create a matrix of test subsurface volumes to permit the assessment of characteristics of each such subsurface volume represented thereby, as well as the characteristics of the interfaces between adjacent test subsurface volumes.

In some embodiments, the method may include successive melt/remelt scans over the same areas, with remelts at different depths of penetration. That is, the method is not limited to a fixed location but may be conducted over an area essentially using three-dimensional melt/remelt patterns that may be obtained through creating prescribed tracks and lines or areas, such as though laser rastering.

It will be appreciated that the number of melts and remelts may be extended from 2 to 3 or more than 3, which may permit conditioning or tempering of the coupon alloy at that location.

In additive manufacture, as the layers are added, the material at a subsurface layer may undergo more than two re-melts in accordance with some variants of the invention. The number of remelts at any given location may be determined by the dimensions of the feed stock powder size; and as long as the depth of penetration is greater, this will recur.

The use of more than melt-re-melt cycles in accordance with the present disclosure may be essential in refractory materials that are difficult to work and that require further conditioning, such as where the heat flux needs to be maintained at higher levels.

In some embodiments, the initial and successive power levels that are applied to bring about the melting and re-melting of the material may be from about 20 W to about 1500 W, though other power levels may be used depending upon the alloy of interest.

The depth of penetration and melting in various embodiments of the method may be in the range of from about 1 μm to about 1500 μm, though other melting penetration depths may be effective depending upon the alloy of interest.

The number of scans in various embodiments of the method may depend upon the number of individual melt profiles and heat affected zones to be generated and may vary from a few as 2 to as many as 1000.

The power level ratio between successive scans in various embodiments of the method may be varied and can be from as little as 1% to 100% of the original/prior scan power.

Similarly, the scan speed ratio between successive scans in various embodiments of the method may be in the range of from about 1% to 100% of the original/prior scan.

Among the several embodiments of the method, the time between successive scans may be in the range of from about 0.0001 seconds to about 10,000 seconds.

The several embodiments of the method may apply an-alloyed article or coupon temperature that may be changed with a secondary heat source prior to and/or between successive scans where the substrate temperature may be in the range of from about −170° C. to about 2000° C.

Other embodiments of the method of the present disclosure may feature a modification of the initial substructure of the article or coupon material, by rapid heating and cooling.

The method of the present disclosure may also entail a procedure that includes the fabrication of alloyed test coupons from candidate alloy compositions and subsequently subjecting these coupons to a thermal cycling regimen described above to generate a simulated thermal history that is typically experienced during the L-PBF build process by powder feedstocks.

The alloy composition may be made by conventional means such as melt casting, induction melting, vacuum or inert gas arc melting, splat quenching, or any other metal forming processes that combine the constituents in elemental or compound form into a single solid, semi-solid, or liquid. The bulk form of the alloy may be sufficiently small that it can be easily manipulated by hand. However, the size of this bulk form does not prevent its use in accordance with the method of the disclosure. If the alloy is relatively large in size, a smaller piece could be sectioned from it. The substructure of this bulk form may consist of a single phase or plurality of phases within a homogeneous to heterogeneous semi solid or liquid state that upon cooling can solidify into a solid bulk product but is large enough to represent the overall alloy composition or chemistry, as well as its structure. This product can vary in overall form from being a rounded button to being a plate to being blocky or a fragment from the larger as-fabricated section.

If processed from an initially liquid state, upon cooling, the internal structure of the now solid bulk product may consist of a single homogeneous phase, comprising a uniform microstructure of equiaxed grains of equal size, shape, texture, and crystallographic orientation to comprising of grains having a range of varying sizes, orientations, shapes, textures or crystallographic relationships to one another. Moreover, the solid bulk product may comprise a plurality of phases that can have varying compositions, with grains having a range of sizes, orientations, shapes, textures or crystallographic relationships to one another. In some embodiments, the alloyed solid bulk product can be treated at elevated temperatures, held for short to extended periods of time, and rapidly cooled (i.e., quenched) to create a more homogeneous, less complex microstructure before being subjected to the simulated thermal processing as those experienced under L-PBF process conditions.

Once a desired initial microstructure has been obtained in the solidified bulk product, in some embodiments it may be sectioned into flat substrate pieces. Further, the surface roughness of this cross-sectional substrate may be reduced sufficiently that it does not interfere with any subsequent sequence of thermal processing steps.

In other embodiments the as-prepared flat surface then may be subjected to simulated scanning conditions which emulate those experienced under the normal 3-D printing fabrication steps. These conditions may entail programming the laser beam to expose the surface in a variety of patterns, along multiple directions at multiple powers, speeds, and dwell times; for example, along a straight line or with overlapping or parallel lines with varying spacing in between or even generating intersecting lines. It is expected that with variations of the total power level, dwell time at one spatial location, and duty cycle of the exposure pattern of the beam, the substrate material beneath each spatial location exposed by the laser beam will interact with photons causing atomic vibration leading to heat generation. The beam conditions at each location are controlled to obtain a direct correlation between the extent (i.e., depth and breadth) of the heat affected zone and the resultant microstructural changes in the same subsurface regions.

The creation of single or multiple laser beam tracks on the article or coupon surface of the material is to simulate the melting behavior experienced during the processing of a layer of loose powder particles. That is, the sequential laser melting-remelting processes described in this disclosure is to very closely approximate those conditions experienced during 3-D print processing. During 3-D printing, as the laser beam is rastered over the surface of the build, each of the particles residing on the topmost surface layer of the powder bed undergoes melting, cools, and fuses to the previously melted layer beneath. With each successive layer added, the laser power is such that not only top surface particles melt but also the layer beneath remelts. In some embodiments, with sufficient laser power, multiple layers could be completely melted and remelted. In some embodiments, if the laser power is too high, it can lead to total volatilization, evaporation, or selective evaporation of some of the constituents. Under some circumstances this may be desirable. Conversely, the method of the present disclosure also may be adapted to function as a procedure for dealloying or functional adjustment of the local composition. Moreover, the laser power, dwell time, and rastering speed conditions may be adjusted to create a new phase by facilitating selective reactions between constituents in the alloy chemical composition. In still other embodiments, multiple laser beams may be used to act upon the substrate simultaneously, either at the same or different locations, in order to bring energy go bear in accordance with the present disclosure.

During the conventional L-PBF process, as the height of the build increases, this melt-remelt process ensures that each particle layer is adequately fused to the layer below producing strong interparticle bonding and eliminating residual porosity, thereby creating integrity and bulk strength in the product build.

In particular, the method of this disclosure facilitates the creation of a substructure modified by simulated thermal cycling that would be also created during the L-PBF process. One of the beneficial aspects of this disclosure is that it requires significantly less material to interrogate than in the conventional L-PBF process. Another aspect of the method of this disclosure is that it permits an elucidation of the evolution of a heat affected zone in a representative volume of material that has a simpler geometry. Yet another aspect of the disclosure is that it does not require the production or acquisition of expensive powder feedstock and reduces the sampling, examination, and evaluation of the interior microstructure of a more complex build. Further, another aspect of the disclosure is that multiple samples can be examined at the same time and subjected to the same or entirely different scanning procedures in the same system as that which would have been used for the actual AM build process. Thus, both the creation of the patterns and their subsequent microstructural examination of the heat affected zones created by carefully constructed but simulated laser raster schedules can completely and effectively describe the repeated melting-remelting processes that occur during the actual 3-D printing build process.

The present disclosure further includes a method to modify an alloy chemistry by melting under simulated additive manufacturing conditions without the need for powder feedstock by: (a) melting the surface or subsurface of an-alloyed coupon at an energy level sufficient to produce a coupon of a comparatively refined or homogeneous distribution of the constituents at a melted depth, (b) under relatively rapid cooling, suppressing extensive grain growth in the molten zone, (c) modifying the re-solidified substructure of a pre-alloyed coupon, (d) redistributing the constituents of a pre-alloyed coupon, and (e) using analytical methods, establishing altered properties in the heat affected zone as compared to the initial substructure of the coupon.

This method may be applied to redistribute second phases from the interiors of grains to the grain boundaries or vice versa, so as to modify the mechanical properties of the alloy.

This method may be carried out using a single line scan that has a constant power level, or through the application of a single line or spot scan with varying laser power levels and duty cycles to vary the depth of penetration along the line.

In other embodiments, the method may be carried out using hatch patterns with overlapping strategies to modify large volumes of the material in the test coupon.

These methods may be carried out using multiple line scans, including multiple line scans that are parallel without overlapping, multiple line scans that are intersecting, and/or multiple line scans that overlap.

The present disclosure further includes a method that comprises the fabrication of test coupons from alloy materials and subjecting them to an energy source at various energy levels, dwell times, and exposure patterns that allows for the evaluation of a single or multiple samples simultaneously, with varying energy levels to cause localized melting of the surface and subsurface, with varying dwell times to cause variations in depths of penetration, with varying dwell times to cause variations in heating/cooling rates, and exposure patterns to emulate an AM build pattern.

Through this method, a modification of the microstructure of the alloy may be employed to create a single phase, or a modification of the microstructure to create cracks and fissures in the molten zone.

DETAILED DESCRIPTION OF DISCLOSED EMBODIMENTS

So that the manner in which the above recited features of the present disclosure can be understood in detail, a more particular description of the disclosure, briefly summarized above, may be had by reference to the embodiments, some of which are illustrated in the appended drawings. It is to be noted, however, that the appended schematic drawings and microphotographs illustrate only some embodiments of this disclosure and are therefore not to be considered limiting of its scope, for the method of the present disclosure may be carried out in other effective embodiments, including less effective but also less expensive embodiments which for some applications may be preferred when scale up is contemplated or funds are limited. These embodiments are intended to be included within the following description and protected by the accompanying claims.

Figure 1:
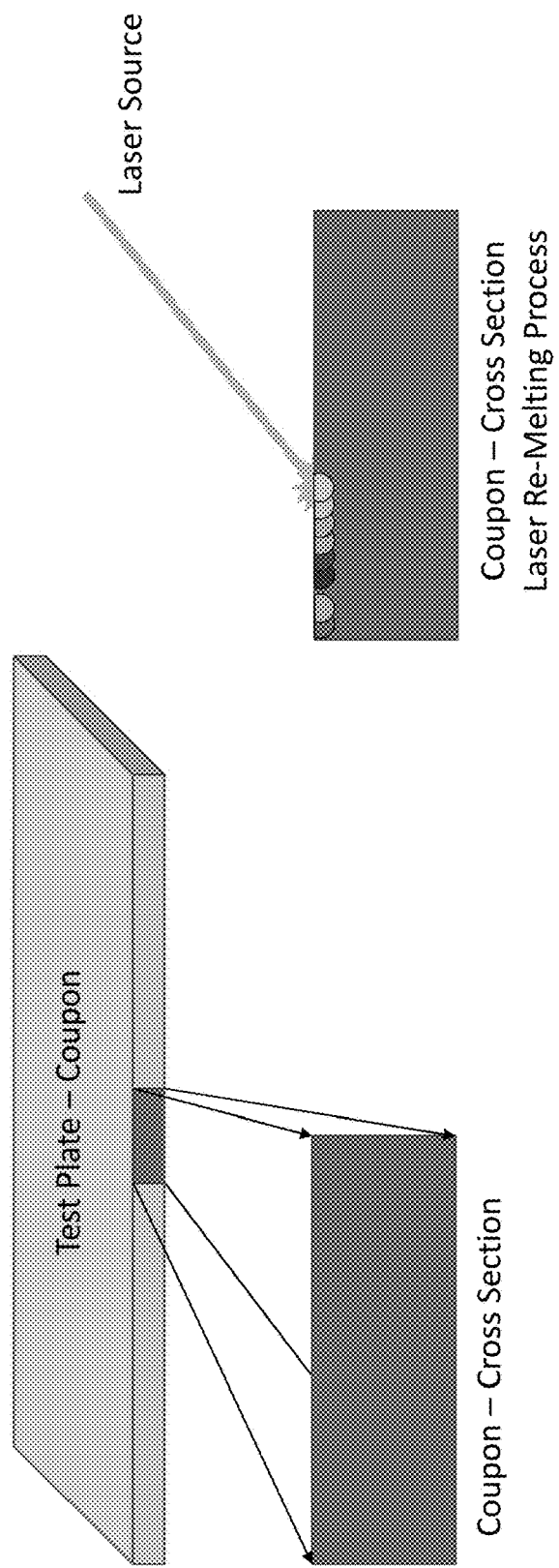
FIG. 1 is a schematic illustrating a test article or coupon that is subjected to the laser-induced melt—re-melt process in accordance with one embodiment of the present disclosure.

FIG. 1 illustrates the simplified schematic of the test article or coupon that is subjected to the laser-induced melt—re-melt process in accordance with one embodiment of the present disclosure.

Figure 2:
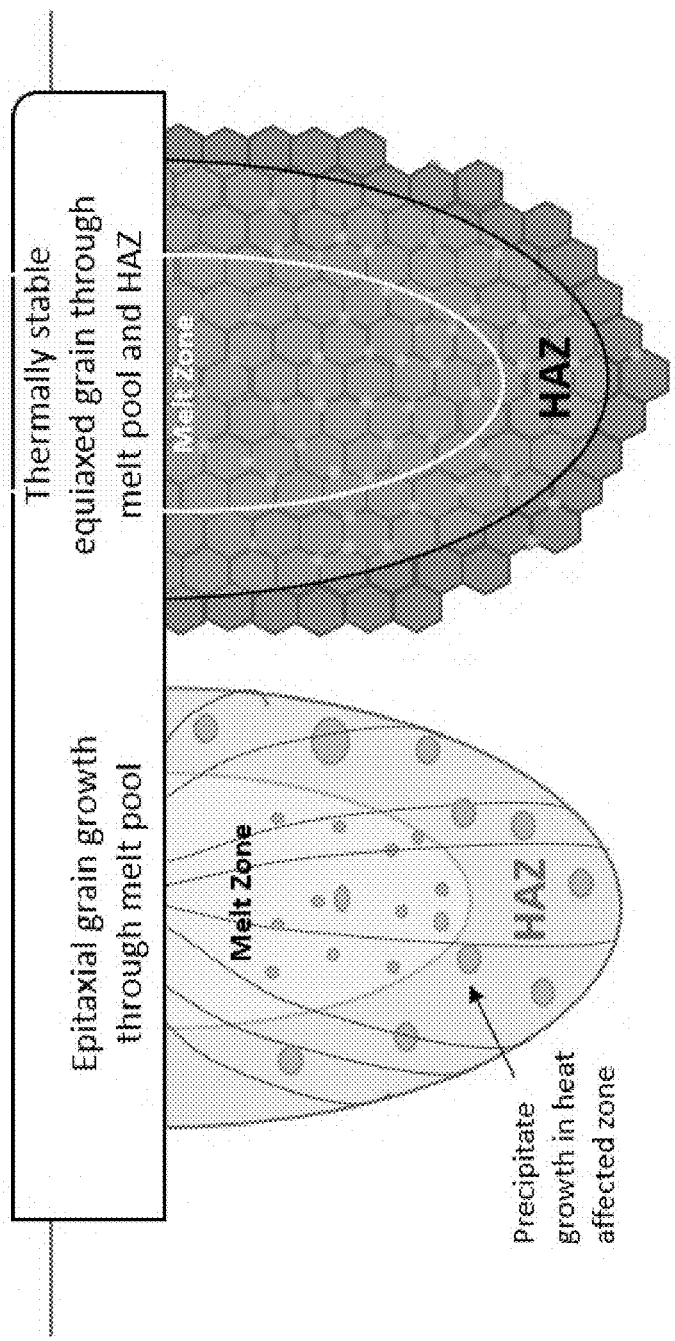
FIG. 2 is a schematic illustrating two types of 3D printed substructures in accordance with one embodiment of the present disclosure.

FIG. 2 illustrates simplified schematics of two types of 3D printed substructures in accordance with one embodiment of the present disclosure. On the left, 2(A), a typical layered substructure includes both a molten and a heat affected zone (HAZ) of a 3D printed material. The zones or volumes comprise epitaxially growing, preferential grains out of the molten zone into the heat affected region surrounding it. For certain compositions, precipitates nucleate in the molten zone, and continue to grow within the cooler heat affected zone. The distribution can change depending on the local heating and cooling rates during the process. On the right, 2(B), the schematic of an idealized substructure is displayed wherein the morphology of grain and precipitates are stabilized and remain uniform throughout the entire molten zone and the heat affected zone surrounding it.

Figure 3:
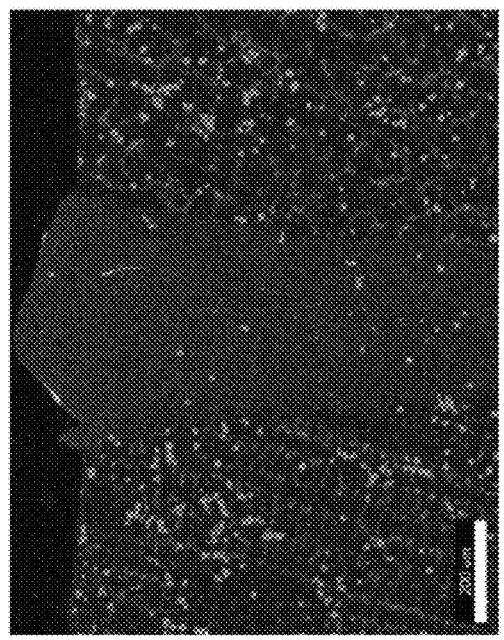
FIG. 3 contains scanning electron micrographs showing the substructure of a typical remelted zone in a test substrate in accordance with one embodiment of the present disclosure.
Figure 3:
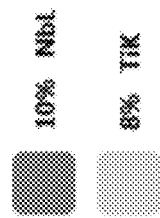
Figure 3:
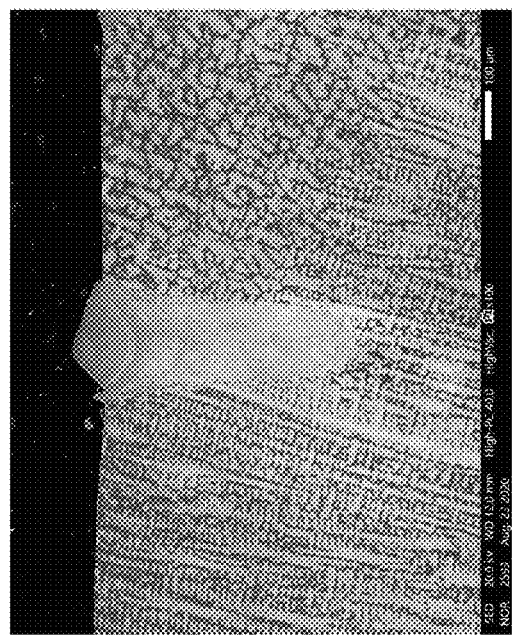

FIG. 3 illustrates the substructure of a typical remelted zone in a test substrate in accordance with one embodiment of the present disclosure. On the left, 3(A) is a scanning electron micrograph of a 95.1Cu-3.1Nb-1.8Ti (wt. %) sample. On the right, 3(B), is the corresponding energy dispersive X-ray spectroscopy (EDS) spectrum dot map showing the distribution of the Nb and Ti elemental constituents.

Figure 4:
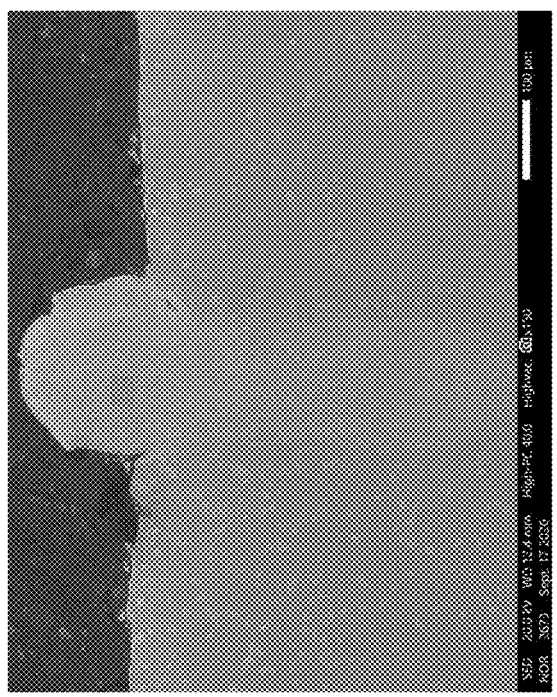
FIG. 4 contains scanning electron micrographs showing the changes of microstructure of the laser re-melted specimen treated in accordance with one embodiment of the present disclosure.
Figure 4:
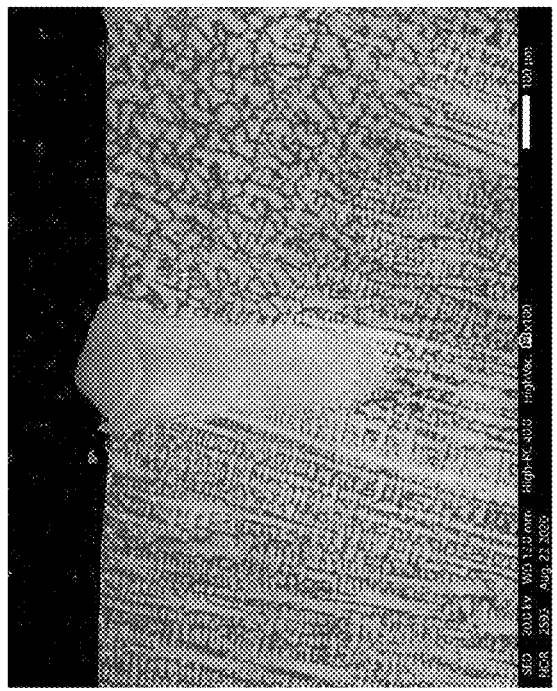
Figure 4:
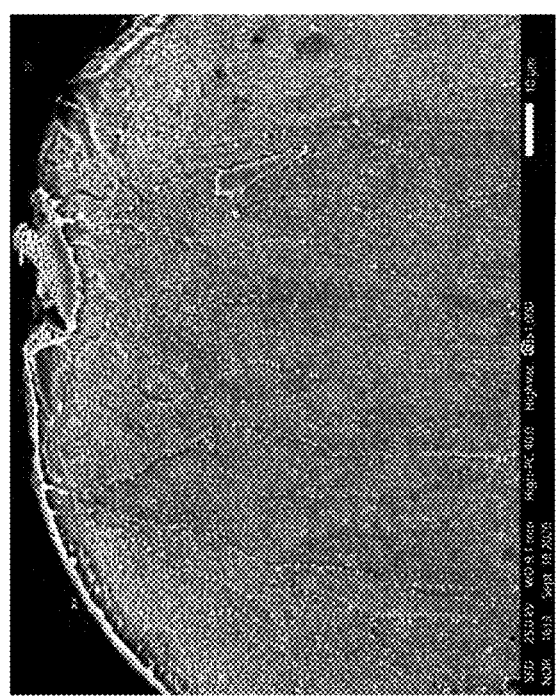
Figure 4:
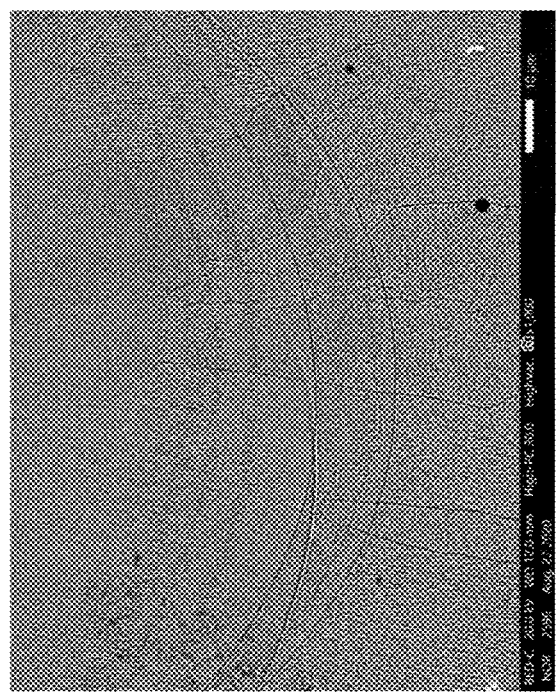

FIG. 4 illustrates the changes of microstructure of the laser re-melted specimen treated in accordance with one embodiment of the present disclosure, and after it was subjected to an 8 hour long heat treatment at 900° C.; 4(A) illustrates the macrostructure of the molten zone of the fillet, and 4(C) illustrates the epitaxially formed grains within the solidified melt. Likewise, 4(B) illustrates the macrostructure of another fillet, and 4(D) illustrates the epitaxially formed grain within the solidified melt near its top. Note in 4(D) the appearance and redistribution of fine precipitates along the grain boundaries.

Figure 5:
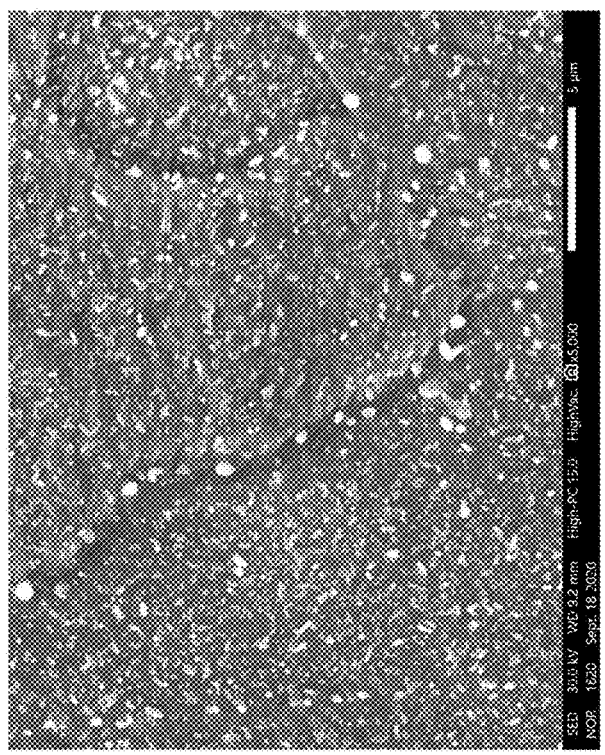
FIG. 5 contains scanning electron micrographs showing the change in the microstructure of the laser re-melted specimen after it was subjected to post-rastering heat treatment at higher magnification in accordance with one embodiment of the present disclosure.
Figure 5:
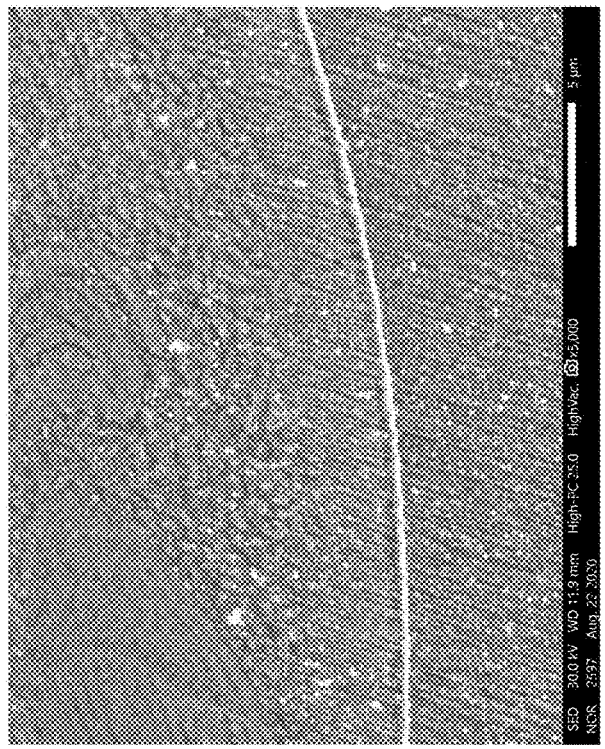

FIG. 5 illustrates the change in the microstructure of the laser re-melted specimen after it was subjected to post-rastering heat treatment at higher magnification in accordance with one embodiment of the present disclosure. Of interest are the changed distributions and sizes of the fine precipitates along the grain boundaries and within their interiors.

Figure 6:
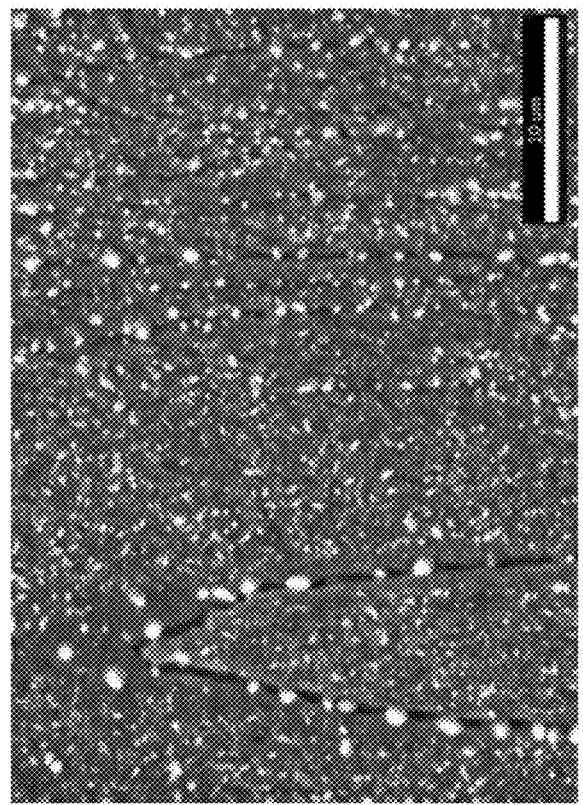
FIG. 6 contains scanning electron micrographs showing the size of the precipitates after heat treatment in accordance with one embodiment of the present disclosure.
Figure 6:
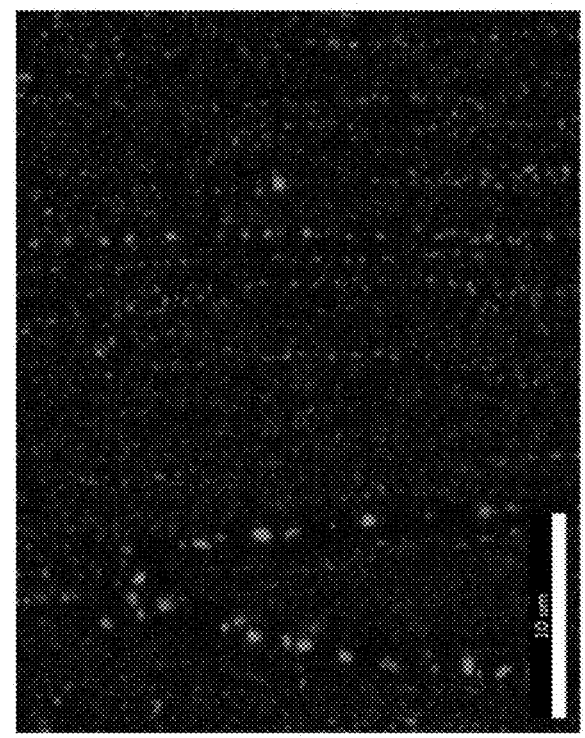

FIG. 6 illustrates the size of the precipitates after heat treatment in accordance with one embodiment of the present disclosure. On the left, 6(A), the image shows at high magnification the grain boundary region of the heat-treated sample. On the right, 6(B) is an EDS dot map showing the distribution of the Nb elemental constituent.

Figure 7:
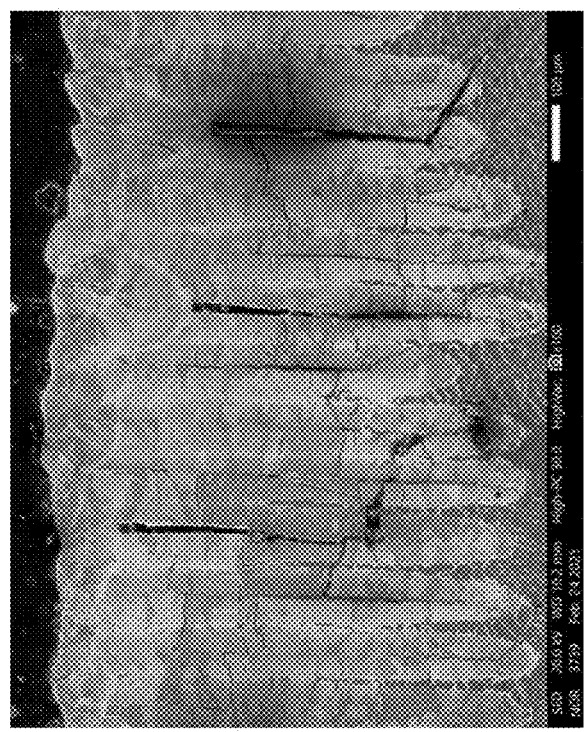
FIG. 7 contains a photograph and scanning electron micrograph showing a typical test article or coupon after it has been subjected to the simulated AM melt-remelt process in accordance with one embodiment of the present disclosure, and the cross-sectional profile of the melted zone beneath the top surface of the article or coupon so treated.
Figure 7:
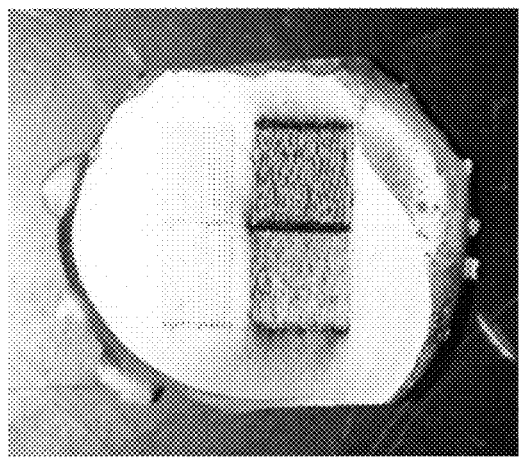

FIG. 7 shows a typical test coupon in 7(A) after it has been subjected to the simulated AM melt-remelt process and the cross-sectional profile in 7(B) of the melted zone beneath the top surface of the article or coupon in accordance with one embodiment of the present disclosure. The image on the left, 7(A), shows non-overlapping parallel single line scans as well as the surface pattern of multiple line scans that overlap using different power levels and scan speeds. The micrograph on the right, 7(B), illustrates the varying penetration depths that can be attained by using various power settings during the melt-remelt process. Note that the interior structure of the molten regions is different from the initial structure of the test coupon.

Figure 8:
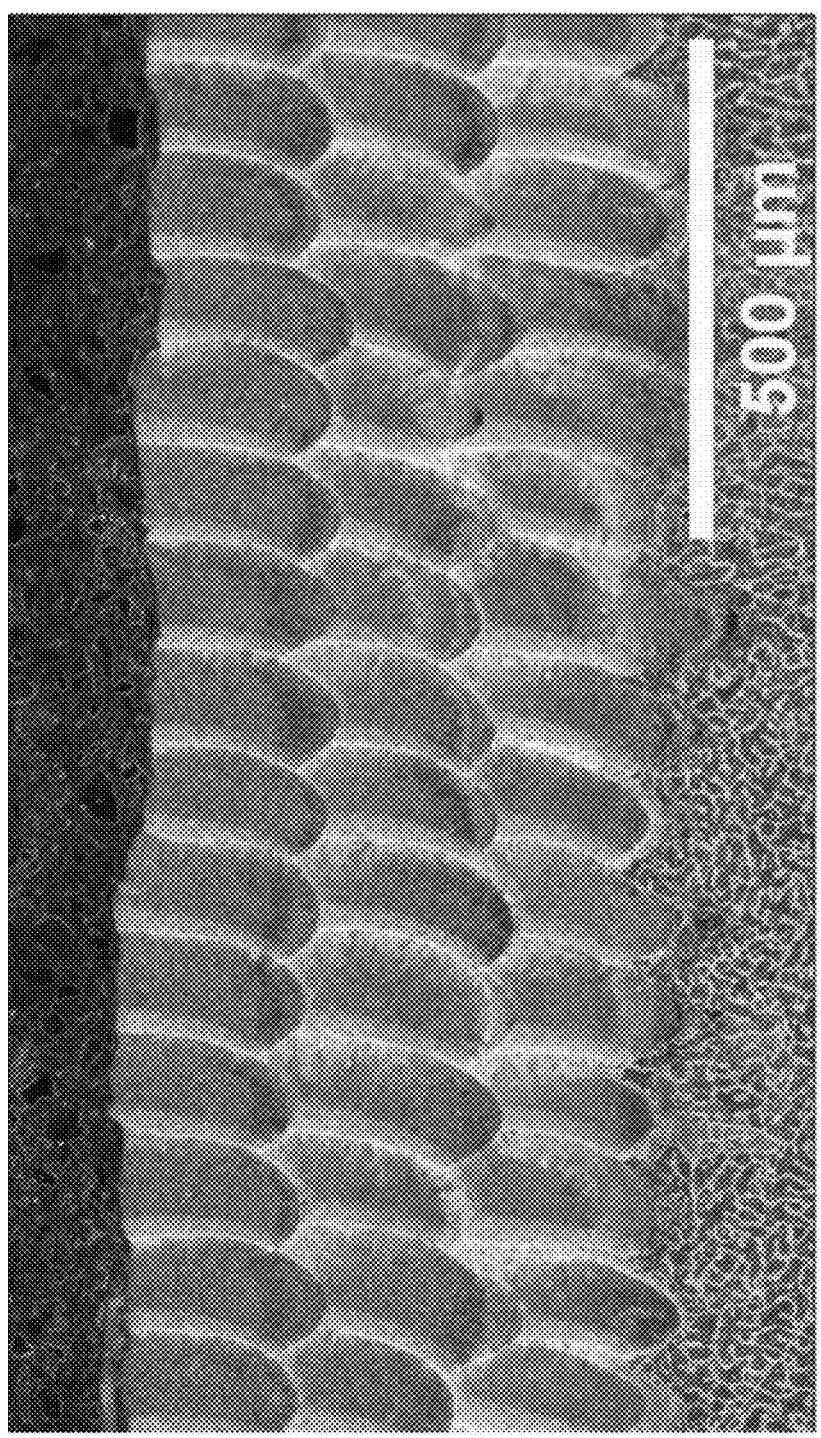
FIG. 8 contains a scanning electron micrograph showing the modification of the subsurface of an exemplary Cu-based alloy with uniformly overlapping melted zones, in accordance with another embodiment of the present disclosure, and clearly revealing internal boundaries.

FIG. 8 illustrates the modification of the subsurface of an exemplary Cu-based alloy with uniformly overlapping melted zones, clearly revealing internal boundaries. As the transverse cross-section (perpendicular to the line scan direction) reveals, the specimen was subjected to a series of overlapping line scans, with decreasing power levels. This material would behave well during the real AM build process; the melted regions do not contain macro-cracks.

Figure 9:
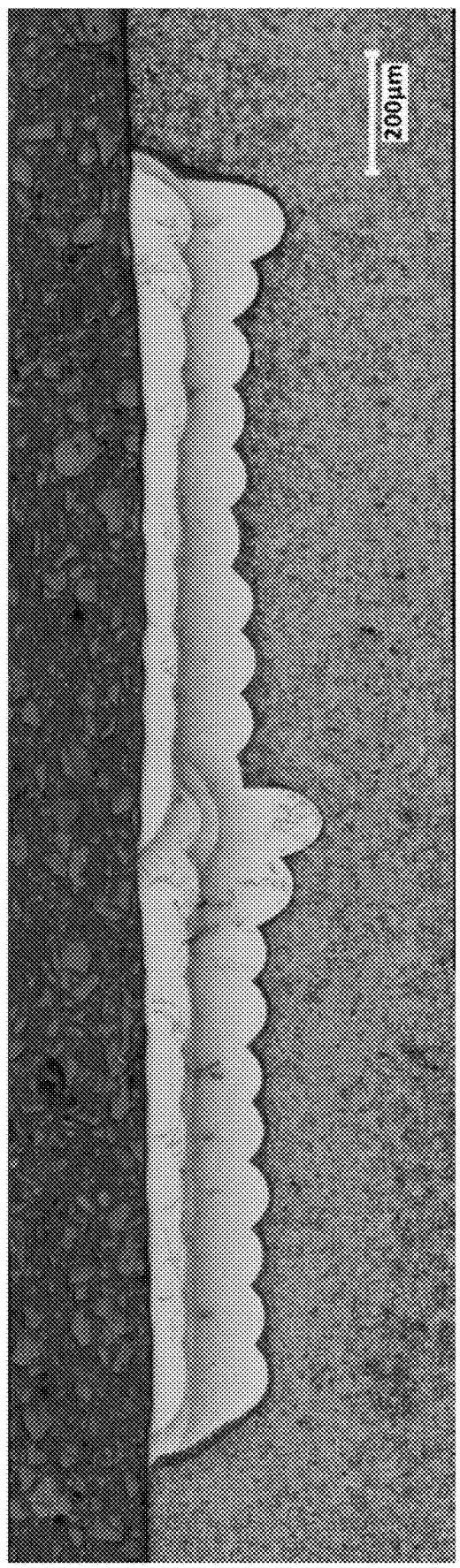
FIG. 9 contains a scanning electron micrograph showing a longitudinal cross-section view (sample sectioned parallel to the line scan direction) of an exemplary S7 tool steel article or coupon subjected to multiple overlapping line scans in accordance with another embodiment of the present disclosure.

FIG. 9 shows a longitudinal cross-section (sample sectioned parallel to the line scan direction) micrographs of an exemplary S7 tool steel coupon subjected to multiple overlapping line scans. Note, that for the given power level, the first line scan penetrated the deepest into the bulk. All subsequent scans were intentionally conducted with lower power levels for shallower penetration depths. This material would not behave well during a real AM build process; the re-melted regions contain macro-cracks.

Figure 10:
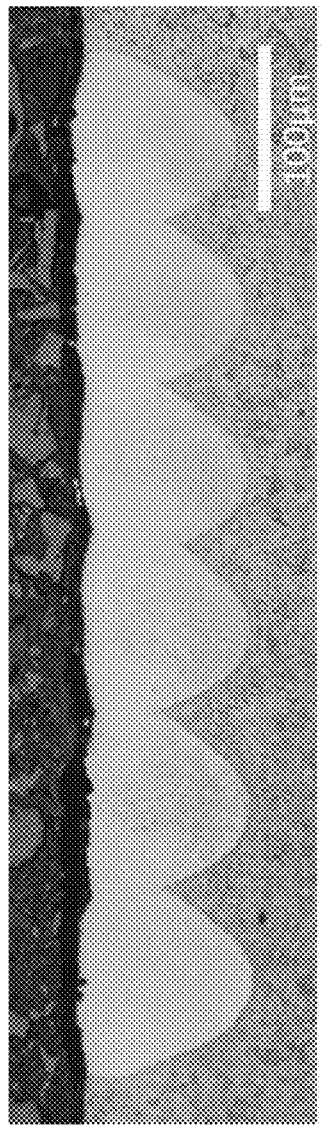
FIG. 10 contains a scanning electron micrograph showing a transverse cross-sectional view of the same exemplary S7 steel coupon that has been subjected to only single minimally overlapping line scans in accordance with another embodiment of the present disclosure.

FIG. 10 shows a transverse cross-sectional micrograph of the same exemplary S7 steel coupon that has been subjected to only single minimally overlapping line scans. The cross-section was taken perpendicular to the direction of the line scans. After a single scan, the interior cracks have not yet developed.

The general sequence of steps utilized in one embodiment of the present disclosure may be summarized as follows:

Step 1: Alloy melting in laboratory scale heating unit or furnace system.

Step 2: Forming or machining the alloy into flat plate.

Step 3: Localized melting the surface at least three energy levels where the first melt produces a deeper melt than any of the subsequent melting events.

Step 4: Thru-thickness sectioning of the as-remelted plate.

Step 5: Performing metallographic preparation and analysis of the cross section of the plate below the melted surface.

Step 6: Examining the region of melted area and the region below the melted area.

The component steps are now described in more detail.

In Step 1, small alloy test ingots, preferably, under 100 grams, are created using laboratory scale furnaces using conventional melt processes. These melt processes may include but are not limited to using laboratory-scale heating units or furnace systems (the actual melting may occur via crucible melting, induction melting, arc melting, or conventional resistance melting.) The melt processes may take place under inert, partially reactive, to reactive atmospheres. The resultant substructure of the ingot may range from being fully homogeneous and uniform to being highly heterogeneous and nonuniform. Regardless of the interior features of the coupon's initial substructure, the steps of the subsequent procedure will likely alter its characteristics.

In Step 2, after cooling and removal from the melting apparatus, the ingot is machined or formed into a flat plate or coupon with a smooth surface finish. As illustrated schematically in FIG. 1, in turn, the finished coupon is then placed into an AM system, and subjected to laser re-melting under a variety of laser power settings and raster scan strategies, dwell times, and speeds. Once a wide and deep enough region of the top surface layer is re-melted, standard metallography is performed on the coupon to prepare it for microstructural examination of the laser melted zone. The suitability of the alloy is then characterized by comparing its microstructure and mechanical properties against a range of property metrics.

The claimed invention herein differs from the methodologies and approaches of traditional material evaluations that are currently used. The novelty of the invention described herein is the fact that it is high throughput, as it allows for a large number of alloy compositions to be tested in the same system at the same time and under the same conditions. This is unlike the traditional method which only allows the testing of only one composition under actual AM printing conditions, which requires a dedicated system and a large quantity of powdered feedstock.

As such, key aspects of the invention also overcome existing limitations of cost and time. Current methods are just too slow and expensive. The new methodology is efficient, low cost, and fast and utilizes readily available processing technology and analysis methods. However, it may be noted that a dedicated 3D test bed is not required to perform this material evaluation method. Any apparatus that has a medium to high power laser system, programmable control system and rastering capability, with an inert cover gas atmosphere would be suitable to carry out the procedures.

In Step 3, the flat test coupon is placed in the AM apparatus and scanned with the laser beam. The intent of the scanning is to cause the metal alloy in the plate to undergo localized melting. Moreover, what is critical is that the first pass over the surface must produce the deepest penetration into the bulk. This accomplishes several effects. In the first, it creates a molten zone that can be post-mortem measured as a function of the incident laser power level and scan rate. In the second, it causes the initial microstructure to fully melt and, depending on the raster rate, will lead to a fully solutionized substructure. In case the initial melt fabrication procedure did not produce a homogeneous and uniform microstructure, this will be critical in emulating the actual AM process. This is because the typical temperature excursions during 3D printing would likely cause complete melting and solidification. If the initial sample was non-uniform or heterogeneous, as may be the case with some powder feedstocks, this process will homogenize them. Regardless, the re-melted and solutionized microstructure is expected to be representative of the alloy material's response to rapid heating and rapid cooling. In the third, based on the thermal characteristics and properties of the alloy, it will establish a direct relationship between the available power levels and the volume of material that can be melted in a reasonable timeframe. These factors are all critical in identifying the required AM printing conditions.

If desired, the initial single laser line- or spot-scan then can be isolated for further analysis or another line scan can be generated directly on top of it. While the intent herein is to generate geometrically simple scan patterns, the method does not preclude more complex geometries and surface topologies. Depending on the simulated geometry of the part, the scan strategy may be altered to include and cover more complex hatch patterns with circular symmetry. However, the unique and non-obvious feature of this invention is the use of multiple scans that re-expose the previously melted region to the laser beam. The intent of the second or third tracks is to emulate the passing of the power beam over an already exposed region of the sample material. This would constitute what occurs during the 3D printing process. Another key aspect of this melt-remelt process is that the level of power input into the melted zone during the second or re-melt pass is that it must be less than that of the power level during the first pass. The use of equal or higher power levels would circumvent the simulation of the AM process. In fact, ideally, during the second or any subsequent passes, the power levels would need to be adjusted and reduced to match the AM procedures as much as possible.

In Step 4, after the scans are completed, the plate is sectioned to facilitate the examination of the subsurface regions for any structural and morphological changes that may have occurred. The examination requires that both transverse and axial cross-sections are taken and are prepared metallograhically.

In Step 5, this preparation necessitates the removal of any surface roughness of the cross-section and its near-mirror finish to allow the subsurface examination of the sample via optical and electron microscopy techniques as well as facilitate microhardness measurements.

In Step 6, the detailed examination entails comparative analysis of the original and heat affected zones, specifically, the un-melted, melted, and re-melted regions of the sample material for apparent structural and morphological changes that may have occurred during the thermal cycling. The analysis may be carried out using a combination of microscopic examination techniques of the substructure that may identify changes in morphology, texture, phase composition, and distribution of the elemental constituents of the alloy. The methods can include but are not limited to micro-computed tomography, optical, scanning, and transmission electron microscopy, energy dispersive X-ray spectroscopy, electron backscatter diffraction, microfocus X-ray diffraction, and nano- to microhardness measurements.

Changes in the resultant substrate substructure could include but are not limited to the formation of coarser or finer grains, dissolution, migration and redistribution of the constituents, separation of phases, and formation and growth of existing or precipitation of new phases from the melt. Further, the crystallographic orientation of the grains could change. There could also be cracks induced from shrinkage or residual stress build up. It is important not to limit the examination to the heat affected zone only. The onset of changes that may occur in regions adjacent to the molten zone may provide information about the thermophysical properties of the alloy and its ability to withstand the extreme thermal excursions during the simulated and actual printing procedures.

The aforementioned steps must be performed in the sequential order listed, however, it is plausible that various steps can be performed out of sequence and with variations. For example, the alloy fabrication step could be altered to drop the alloy into a liquid medium or onto a different surface than a plate or crucible. Or not dropped at all and just allowed to solidify via natural cooling.

Likewise, instead of performing all the steps, one could test the performance and properties of the new alloy by other means, such as microhardness or wear resistance measurements.

Similarly, the localized melting could be performed with an electron beam instead of a laser beam.

In addition to using the property evaluation methods described herein to quantify the utility of the new composition, there are other relevant physio-chemical methods to determine the alloy's possible suitability in meeting the required AM printing performance benchmarks. These can include post-melting heat treatment studies to determine the rates of growth of the as-formed grains and of precipitates.

EXAMPLES OF THE DISCLOSED METHODS

Key details of the disclosed methods applied to specific alloy compositions are described in the following sections. Additionally, the characteristic features of the post-melted and re-melted regions of the exemplary alloy compositions are identified and delineated as well.

In the conventional L-PBF approach with a new composition, powder feedstock from a hopper is fed onto a movable bed and a prescribed structure is built as the laser beam scans parts of the surface. As the dimensions of the structure grow, the powder particles on the top layer within the structure are melted and re-melted. Instead of this laborious process, this invention eliminates the need for powder feedstock, most of which does not participate in the melt cycle. Rather, in Step 1, the user works with lesser quantities of the constituent elements to melt and combine all of the individual elements into a homogenous solution. This may require processing temperatures much higher than just the melting of the components. This molten solution should then be cooled (or quenched) as quickly as possible. The preferred method would be to drop the molten solution on to a chilled plate. This cooling rate will still be slow compared to laser melting but is preferred to a slowly cooled process.

Forming or machining a flat plate from the test alloy composition (Step 2) allows for better control over the energy delivered during the laser re-melting process. The last re-melting step (Step 3) should be performed at many speeds and power levels to ensure that the results are not only attainable in a single combination, but also to identify key trends with respect to speed or power level. See FIG. 1. This process emulates the conventional build process without the need for the powder feedstock. While the initial, as-cooled substructure within the plate may not be the same as that built from powder particles, in the end, after being exposed to laser rastering, the top surface of the plate will undergo the same melting and cooling cycle as in the conventional process. As such, it is expected that the local atomic rearrangement in the two respective processes would be the same. Specifically, the range of setting should vary for laser scans from 100 mm/s to 3000 mm/s, and power levels of 100 W to 1000 W. Scan raster plans should also include different patterns such as parallel melts with overlap.

Finally, the microstructure examination criteria (applied in Steps 5 and 6) for a successful evaluation will change based on the alloy being developed. In some cases, a heat treatment may be performed on the laser remelted coupon prior to examination. Hardness testing may be used in conjunction with microstructure analysis.

One would choose a series of elements (at least two), melt them sufficiently in an arc melting furnace or similar device, and drop the melt onto chilled copper crucible/plate.

Laser re-melting of the machined plate could be performed in a commercial L-PBF system such as commercially available Aconity3D or AconityONE AM systems. However, any other system would be able to perform the re-melting operations as well. The work could also be performed in non-AM systems, such as a laser cutting or laser welding system; as long as the system can provide a rastered source of power that is sufficient to melt the surface layer. Atmosphere control may be employed to prevent oxidation and in some embodiments the ability to program the laser scanning parameters. But in other embodiments that may not be necessary.

The metallography is used to determine the substructure and whether the alloy composition met successfully the objectives of the alloy design criteria. For example, one may look to develop an alloy with an equiaxed grain structure in the re-melted region with or without uniformly distributed nano-precipitates. See FIG. 2.

Steps 1, 2, and 4 are always necessary to implement this invention. Also, some forms of steps 5 and 6 to quantify if the alloy is "good" are also required. However, in addition to those steps identified above, other property quantification methods could include thermal properties testing, mechanical properties testing, chemical resistance testing, and biocompatibility testing.

One would use this high-throughput method to quickly and cost effectively create new series of alloy with a range of compositions for L-PBF. Specifically, using this novel approach, the user would be able to develop and optimize alloy composition for a specific application much more rapidly and efficiently compared to empirical trial-and-error iterative approaches. An example of this process would be using it to design and develop a new alloy composition or chemistry for turbine blades or a new alloy for heat exchangers.

Example 1: Copper-Niobium-Titanium Alloy

In one example, an exemplary copper-niobium-titanium (Cu—Nb—Ti) alloy with a nominal composition of 95.1Cu-3.1Nb-1.8Ti (wt. %) has been subjected to single line scan using the laser melting-remelting procedure. The elemental constituents were arc melted under argon, and the resultant button was fashioned into a flat plate-shaped substrate. The substrate was placed in a AconityONE AM system and subjected to the testing schedule. A total of three overlapping single line laser scans were made. In the first, the laser speed was 500 mm/s with a laser power of 500 W; in the second scan the laser speed was 1000 mm/s with a laser power of 900 W; and, in the third scan the laser speed was 1200 mm/s with a laser power of 350 W. These speeds and power levels are typical in a 3D printing run. The intent was to generate a deep, penetrating molten fillet within the material substrate. FIG. 3 shows a transverse cross section of the line scan illustrating the effect of the multi-melt by the laser on the material's substructure. The as-arc-melted regions outside of the molten zone contain grain which are dendritic, highly variable, but generally consisting of dendritic arms with varying dimensions. The interior of the molten zone appears much more uniform. The image in the right shows that, under the influence of the laser, the secondary elemental constituents of Nb and Ti have been redistributed and their distributions have become much more uniform and finely dispersed.

The laser re-melted substrate was also subjected to an 8-hour long heat treatment at 900° C. under rough vacuum. FIGS. 4 and 5 reveal that the grain morphology within the laser re-melted region is consistent with those typical of 3D printed materials. The grains are epitaxial, vertically oriented with large aspect ratios. Also evident from a comparison of the images, especially at higher magnification is that the precipitates in the heat-treated region grow. The increase in precipitate size is about five-fold, but even the largest of the precipitates remain submicrometer, about 500 nm. FIG. 6 reveals that the Nb-containing precipitates accumulate at the epitaxially formed grain boundaries.

Example 2: Multi-Scan Hatch Patterns of Various Materials

To create the test coupon, elemental constituents were arc melted under argon, and the resultant button was fashioned into a flat plate-shaped substrate. On the left side of FIG. 7 illustrates the top surface of a typical test coupon that has been subjected to two types of rastering schedules. In the upper test grid patterns, the single line melts are parallel and do not overlap. In the bottom test grid patterns, the line scans do overlap and the procedure melts-re-melts the sample bulk beneath the surface. The differences in the external appearance of these test grids are attributed to different scan speeds and laser power levels. On the right side of FIG. 7, the scanning electron micrograph illustrates the resultant substructure of the material beneath the surface. It reveals that the initial line scans penetrate the deepest into the test coupon and the subsequent re-melts mostly modify the region near the surface only. The melt-re-melt process causes the microstructure to undergo considerable change which is very different from that of the initial microstructure seen beneath the molten columns. The process also creates defects such as voids and cracks within the melted zone.

In another example a larger material volume is interrogated in a Cu-based alloy. The elemental constituents were arc melted under argon, and the resultant button was fashioned into a flat plate-shaped substrate. The substrate was subjected to laser hatching melts where each vector was 0.1 mm from the previous, representing a hatch spacing commonly seen in L-PBF AM. The hatching pattern was repeated three times, where each successive melt was delayed 60 seconds (note, this delay could be 0.1 second to 3600 seconds) to represent a nominal layering time seen in L-PBF processing. The first melt was performed with laser power 809 W and scan speed of 300 mm/s resulting in a linear energy of 2.72 J/mm, a second melt was performed at 981 W and a scan speed of 600 mm/s resulting in a linear energy of 1.44 J/mm, and a third scan at an even lower energy of 801 W and a scan speed of 900 mm/s resulting in a linear energy of 0.79 J/mm. FIG. 8 reveals the cross-section of the plate with a resultant microstructure that is highly representative of what is commonly seen in L-PBF AM parts where successive melt pools overlap and are clearly visible. The micrograph is rich with information that can be used to determine alloy viability in L-PBF and the effectiveness of the chosen laser melting parameters. The micrograph allows for precise quantification of melt pool depths, widths, overlapping depths, microstructure evolution along the melt boundaries, grain size, precipitate size, distribution among other microstructural characteristics.

Example 3: Non-Weldable Tool Steel

In another example of an alloy that is known to be crack prone or not feasible in L-PBF was subjected to a variety of laser melting scans. The alloy seen in FIG. 9 is an S7 tool steel purchased from a raw material supplier in a bar stock form. This example shows that the method can be used to evaluate printability of any material including traditionally processed alloys as well as evaluation of novel alloys. The S7 tool steel sample was subjected to a laser hatching pattern with hatch spacing of 0.1 mm and 7 remelt cycles at three energy levels. The first pass was performed at the highest energy 3 times then the energy deposition rate was reduced by increasing the laser speed and melted 3 more times, then a single pass made at a final and lowest energy was performed. As seen in FIG. 9, the sample showed significant cracking verifying that the small melt volume is sufficient to evaluate the cracking susceptibility of difficult-to-process alloys.

FIG. 10 shows the results from a single layer of 0.1 mm hatching space under equivalent processing conditions to the final lowest energy that was used for the sample shown in FIG. 9 on the same S7 tool steel substrate, but only single molten fillets were created without overlap which do not reveal any cracking. This illustrates that while the material appears to melt without any cracking issues at lower power levels, internal stresses do accumulate, especially higher power levels and number of melt-remelt cycles. The case with S7 tool steel proves the importance of the multiple remelts.

We claim:

1. A method of producing powdered feedstock for melt-based additive manufacture by evaluating and modifying the substructural features of a pre-alloyed bulk material having predefined chemical composition, comprising the steps of:
   a. melting a defined region on the surface of a coupon of the pre-alloyed bulk material having a predefined chemical composition, using a laser at a first energy level thereby creating a first subsurface volume having a first depth;
   b. obtaining a first set of structural modification measurement data associated with the first subsurface volume after allowing the first subsurface volume to solidify;
   c. re-heating the defined region on the coupon using the laser at a second energy level thereby creating a second subsurface volume having a second depth, wherein the second depth may be deeper or shallower than the first depth;
   d. obtaining a second set of structural modification measurement data associated with the second subsurface volume after allowing the second subsurface volume to cool to a first temperature;
   e. determining whether the first and second subsurface volumes comprise one or more desirable structural characteristics, wherein the one or more desirable structural characteristics comprise the following:
      i. dissolution of the constituent elements, separation of the constituent elements, redistribution of the constituent elements, separation into phases of constituent elements;
      ii. changes in grain morphology, grain size, or grain size distribution;
      iii. prior precipitates of constituent elements, changes in precipitate size, and precipitate spatial distribution;
      iv. lack of defects such as cracks, fissures, and voids;
      v. changes in crystallographic texture;
      vi. changes in microhardness; and
   f. rendering the pre-alloyed bulk material comprising the one or more desirable structural characteristics into a fine-grained, homogenous substructure having uniform composition.

2. A method according to claim 1, wherein the defined region is pre-heated with a secondary heat source prior to melting.

3. A method according to claim 1, comprising the additional step of re-melting the defined region at a third energy level thereby creating a third subsurface volume having a third depth.

4. A method according to claim 1, wherein between two and four energy sources are used to create said subsurface volumes.

5. A method to create a powdered feedstock suitable for melt-based additive manufacturing from a pre-alloyed bulk material having a range of predetermined chemical compositions comprising the steps of:
   a. melting a defined region on a surface of a coupon of pre-alloyed bulk material over a plurality of cycles using a laser, wherein a unique laser energy level, heading, duration, scan speed, and scan pattern is associated with each cycle such that each cycle generates a defined subsurface volume comprising a set of structural modifications;
   b. obtaining structural modification measurement data associated with each defined subsurface volume after allowing the defined subsurface volume to solidify;
   c. rendering pre-alloyed bulk material possessing a set of structural modifications into a powder feedstock, wherein the set of structural modifications are selected from the group consisting of:
      i. the dissolution, separation, and redistribution of the constituent elements, phases, and prior precipitates;
      ii. changes in grain morphology, size, or size distribution;
      ii. changes in precipitate size, size distribution, and spatial distribution;
      iv. appearance of defects such as cracks, fissures, and voids;
      v. changes in crystallographic texture; and
      vi. changes in microhardness.

6. The method according to claim 1, using a pre-alloyed coupon, comprising a single or multiple elemental or compound precursors formed into said article.

7. The method according to claim 1, wherein the pre-alloyed coupon material consists of a single or multiple elemental or compound precursors combined into an article of bulk composite alloy, using metallurgical methods which include melt-cast, induction melting, vacuum or inert gas arc melting, splat quenching, and re-melting methods.

8. The method of modifying the substructure of an article of pre-alloyed bulk material using the method according to claim 5, of a pre-alloyed coupon, comprised of single or multiple elemental or compound precursors formed into said article through any of the metallurgical methods according to claim 7, and following the evaluation of its structural qualities according to the method of claim 5.

9. The method of claim 1, wherein the second energy level is equal to the first energy level.

10. The method of claim 1, wherein the defined region is melted using the laser moving at a first scan speed, and the defined region is re-melted using a laser moving at a second scan speed.

11. The method of claim 5, wherein the unique laser energy level associated with one or more succeeding cycles in the plurality of cycles is the same.

12. The method of claim 5, wherein the laser moves at a scan speed that is the same as that associated with one or more previous cycles of the plurality of cycles.

13. The method according to claim 5, wherein the pre-alloyed bulk material comprises single or multiple elemental or compound precursors.

14. The method according to claim 1, wherein the modified pre-alloyed coupon after the evaluation of its substructure characteristics comprises of an average composition with no greater than 5 atomic percent variation.

15. The method according to claim 1, wherein the modified pre-alloyed coupon after the evaluation of its substructure characteristics comprises grains no larger than 10 micrometers.

16. The method according to claim 1, wherein the modified pre-alloyed coupon after the evaluation of its substructure characteristics comprises grains having a grain size which does not vary by more than 40%.

17. The method according to claim 1, wherein the modified pre-alloyed coupon after the evaluation of its substructure characteristics comprises a crystallographic texture with less than 20% orientation variation.

18. The method according to claim 1, wherein the modified pre-alloyed coupon after the evaluation of its substructure characteristics contains no coarse precipitates with dimensions of greater than 5 micrometers.

19. The method according to claim 1, wherein the modified pre-alloyed coupon after the evaluation of its substructure characteristics contains no coarse precipitates with dimensions of greater than 1 micrometer.

20. The method according to claim 1, wherein the modified pre-alloyed coupon after the evaluation of its substructure characteristics has a minimal defect content without cracks, fissures, or voids.

* * * * *